United States Patent
Richelsoph

[11] Patent Number: 5,964,760
[45] Date of Patent: Oct. 12, 1999

[54] SPINAL IMPLANT FIXATION ASSEMBLY

[75] Inventor: Marc Richelsoph, Memphis, Tenn.

[73] Assignee: Spinal Innovations, Bartlett, Tenn.

[21] Appl. No.: 08/831,112

[22] Filed: Apr. 1, 1997

Related U.S. Application Data

[63] Continuation-in-part of application No. 08/734,520, Oct. 18, 1996, Pat. No. 5,863,293.

[51] Int. Cl.⁶ .................................................. A61B 17/56
[52] U.S. Cl. ............................................... 606/61; 606/73
[58] Field of Search .................. 606/61, 73, 71, 606/70

[56] References Cited

U.S. PATENT DOCUMENTS

| | | | |
|---|---|---|---|
| 5,005,562 | 4/1991 | Cotrel | 128/69 |
| 5,207,678 | 5/1993 | Harms et al. | 606/61 |
| 5,217,497 | 6/1993 | Mehdian | 623/17 |
| 5,257,993 | 11/1993 | Asher et al. | 606/61 |
| 5,360,431 | 11/1994 | Puno et al. | 606/72 |
| 5,443,467 | 8/1995 | Biedermann et al. | 606/73 |
| 5,476,464 | 12/1995 | Metz-Stavenhagen et al. | 606/61 |
| 5,480,401 | 1/1996 | Navas | 606/61 |
| 5,549,608 | 8/1996 | Errico et al. | 606/61 |
| 5,554,157 | 9/1996 | Errico et al. | 606/61 |
| 5,586,984 | 12/1996 | Errico et al. | 606/61 |
| 5,607,426 | 3/1997 | Ralph et al. | 606/70 |
| 5,669,911 | 9/1997 | Errico et al. | 606/73 |
| 5,863,293 | 1/1999 | Richelsoph | 606/61 |

FOREIGN PATENT DOCUMENTS

| | | | |
|---|---|---|---|
| 2682280 | 4/1993 | France | 606/61 |
| 195 09 332 C1 | 8/1996 | Germany . | |
| WO 91/01691 | 2/1991 | WIPO . | |

Primary Examiner—Michael Buiz
Assistant Examiner—Julian W. Woo
Attorney, Agent, or Firm—Kohn & Associates

[57] ABSTRACT

A spinal implant fixation assembly includes a bone fixation member, such as a screw or hook for fixation to a bone. A rod receiving seat is operatively connected to the bone fixation element for seating a portion of a rod therein. A locking mechanism, in the form of a nut and locking ring engage the rod receiving seat for forcing an inner wall of the rod receiving seat to contour around and engage the rod seated therein and for locking and fixing the rod relative to the inner housing. In one embodiment, the locking ring secures a head portion of the bone fixation element within the assembly. A method is also provided for locking the rod to a bone by fixing a rod seating member to a bone and seating a portion of a rod within a substantially U-shaped seat of the seating member. The rod is then locked within the U-shaped seating member while engaging and contouring at least a portion of the U-shaped seat about the rod. The assembly further includes a screw head receiving insert for obtaining a head of screw therein. The insert is moveable within the assembly between a locked position entrapping the screw head and an unlocked position wherein the screw head enters or escapes.

29 Claims, 4 Drawing Sheets

SPINAL IMPLANT FIXATION ASSEMBLY

This application is a continuation-in-part of application U.S. Ser. No. 08/734,520, filed Oct. 18, 1996, now U.S. Pat. No. 5,863,293, issued Jan. 26, 1999.

TECHNICAL FIELD

The present invention relates to a implant fixation system and locking mechanism. More particularly, the present invention provides a locking mechanism, which can be multi-planar or fixed, for securing a rod to an implant.

BACKGROUND OF THE INVENTION

Stabilization of the spine for various conditions, including degenerative disc disease, scoliosis, spondylolithises and spinal stenosis often require attaching implants to the spine and then securing the implants to spinal rods. Such spinal fixation devices can immobilize the vertebrae and can alter the alignment of the spine over a large number of vertebrae by means of connecting at least one elongate rod to the sequence of selected vertebrae. Such rods can span a large number of vertebrae such as three or four. However, the spine anatomy rarely allows for three or more implants to be directly in line. In order to allow for this irregularity, the rod must be contoured to the coronal plane. With anatomical curvature in the saggital plane found in the lumbar spine, the rod has to be contoured in both planes, requiring considerable effort and surgical time.

For example, the U.S. Pat. Nos. 5,554,157, issued Sep. 10, 1996, 5,549,608 issued Aug. 27, 1996, and 5,586,984 issued Dec. 24, 1996, all to Errico et al. disclose polyaxial locking screw and coupling element devices for use with rod fixation apparatus. The '157 patent discloses a coupling element including an interior axial passage having an interior surface which is inwardly curvate at the lower portion thereof such that it comprises a socket for polyaxially retaining a spherical head of a screw. The coupling element further includes a pair of vertically oriented opposing channels extending down from the top of the coupling element which define therebetween a rod receiving seat. The channel further provides the walls of the upper portion to a pair of upwardly extending members, each including an exterior threading disposed on the upper most portion thereof for receiving a locking nut. During the implantation of the assembly, the locking nut seats against the top of the rod which in turn seats on top of the screw head. The nut causes the rod to be locked between the nut and screw and the screw to be locked in the socket.

The '608 patent discloses a modification wherein a locking ring is disposed about the exterior of the lower portion of the coupling element and provides an inward force on an outwardly tapered portion upon downward translation thereof causing the interior chamber to crush lock a screw head therein to eliminate the polyaxial nature of the screw element coupling.

The '984 patent discloses a polyaxial orthopedic device including a cutter element having a tapered lower portion including a slotted interior chamber in which a curvated head of a screw is initially polyaxialed disposed. The coupling element includes a recessed for receiving a rod of the implant apparatus. A locking ring is disposed about the lower portion of the coupling element and provides an inward force on the outwardly tapered portion upon downward translation thereof. The vertical slots are caused to close and crush and thereby locking the screw head within the inter chamber thereof.

In the prior art embodiments, the locking mechanism locks both the rod and screw head simultaneously. No prior art patent allows for the spherical head of the screw to be locked at a desired angle prior to rod insertion. Likewise the only surface locking the rod in place is the surface between either the seat and a locking nut or the rod entrapped between a locking ring and the seat.

It would be desirable to increase the area of contact of the locking mechanism about the rod as this is a high stress site secured only by a friction fit. It would also be desirable to lock the screw head in place prior to fixation of the rod.

SUMMARY OF THE INVENTION

In accordance with the present invention, there is provided a spinal implant fixation assembly including bone fixation means for fixation to a bone and rod receiving means operatively connected to the bone fixation means. The rod receiving means includes a first seat having an inner wall for seating a portion of a rod therein. The assembly further provides locking means engaging the rod receiving means for forcing the inner wall to contour around and engage the rod seated therein and for locking and fixing the rod relative to the inner housing.

The present invention further provides a method for locking a rod to a bone by the steps of fixing a rod seating member to a bone and then seating a portion of a rod within a substantially U-shaped seat of the seating member. The rod is locked within the U-shaped seat while engaging in contouring at least a portion of the U-shaped seat about the rod.

The present invention further provides a spinal fixation assembly including screw head receiving means for retaining a head of a screw therein. The screw head receiving means is moveable within the assembly between a locked position entrapping the screw head and an unlocked position wherein the screw head enters or escapes.

A method is further provided for retaining a screw head in a spinal fixation assembly by inserting a screw head into an expanded pocket of an insert contained within a first portion of an internal portion of a body member wherein the internal portion includes the first portion which is radially outwardly recessed relative to a second portion and then moving the insert into the second portion which compresses the pocket of the insert into a contracted condition to fixedly engage the screw head within the pocket.

BRIEF DESCRIPTION OF THE FIGURES

Other advantages of the present invention will be readily appreciated as the same becomes better understood by reference to the following detailed description when considered in connection with the accompanying drawings wherein.

DETAILED DESCRIPTION OF THE FIGURES

Figure 1:
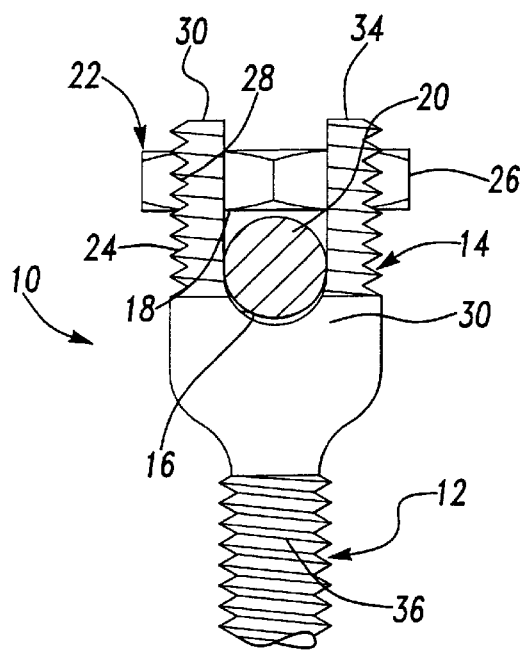
FIG. 1 is a side view partially in cross section of a first embodiment of the present invention.

A spinal implant fixation assembly constructed in accordance with the present invention is generally shown at 10 in FIG. 1. Similar structures amongst the several embodiments are shown by primed numbers in the various Figures.

More specifically, referring to the first embodiment of the present invention generally shown at 10 in FIG. 1, the assembly 10 includes a bone fixation element generally shown at 12 for fixation of the assembly 10 to a bone. A rod receiving mechanism is generally shown at 14 and is operatively connected to the bone fixation element 12. The rod receiving mechanism 14 includes a seat 16 having an inner wall 18 for seating a portion of a rod 20 therein. A locking mechanism generally shown at 22 engages the rod receiving mechanism 14 for forcing the inner wall 18 to contour around and engage the rod 20 seated therein and for locking and fixing the rod 20 relative to the assembly 10. In this manner as the locking mechanism 22 forces the inner wall 18 to contour around and engage the rod 20 seated therein, there is increased surface to surface contact and therefore increased frictional engagement between the seat 16 and rod 20 thereby providing a more effective frictional contact. That is, the inner wall 18 of the seat 16 is compressed against the rod 20. The locking mechanism 22 is also seated against the rod 20. However, unlike prior art assemblies discussed above, the surface area engaging against the rod 20 is vastly increased over the prior art which increases the assembly to rod holding power.

More specifically, the rod receiving mechanism 14 includes a tapered outer surface 24. As shown in the several embodiments, this outer surface 24 can be threaded. However, other means for securing the locking mechanism 22 can be used to achieve the same results. Preferably, the locking mechanism 22 is in the form of a nut member 26 having an inner surface 28, which can be threaded for use with the threaded outer surface 24 of the rod receiving mechanism 14, for being forced over and engaging the outer surface 24 and inwardly deflecting the rod receiving mechanism 14 about the seat portion 16 as the locking member 26 further engages the tapered outer surface 14.

Referring more specifically to the rod receiving mechanism 14, it includes a body portion 30 having two arms 32,34 extending therefrom and being substantially parallel relative to each other. The two arms 32,34 and the body portion 30 form a U-shaped inner surface defining the seat portion 16 thereof. Also, the arms 32,34 have the tapered threaded surface 24 about the outer surface thereof. Thus, as the locking mechanism 22 in the form of the nut member 26 is threaded over the tapered outer surface 24 of the arms 32,34, the nut member 26 compresses the arms 32,34 against a rod member 20 disposed within the seat 16. As stated above, this provides a vastly increased surface area engagement between the seating surface 16, inner walls 18 and rod member 20. The arms 32,34 provide for flexibility, yet are sufficiently rigid to maintain structural integrity.

The tapered threaded portion 24 in combination with the nut member 26 provide a self-locking mechanism for securing the rod 20 thereto. By self-locking, it is meant that mere threading of the nut member 26 on the tapered surface 24 locks the nut member 26 in place. This locking mechanism is vibration resistant and has not been previously used in spinal implants. In combination with the other aspects of the present invention, the self-locking mechanism provides convenience of use and secure locking of the system along with flexibility of attachment of the rod and implant.

Figure 2:
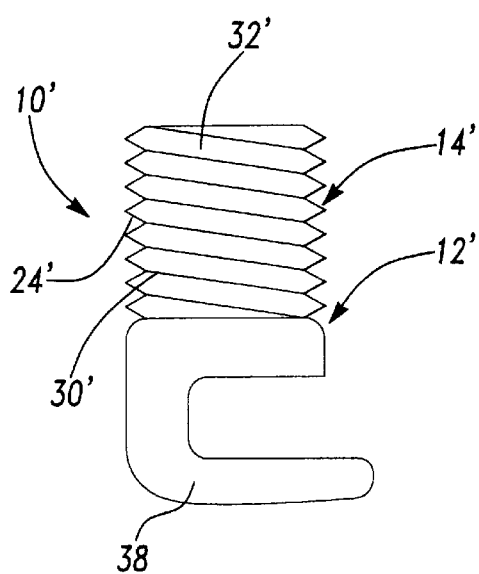
FIG. 2 is a side view of a second embodiment of the present invention.

In the first embodiment shown in FIG. 1, the bone fixation mechanism 12 is shown as a screw portion 36 extending integrally from the body portion 30. The body portion 30 includes a longitudinal axis. The bone fixation element 12, whether it is a screw portion as shown in FIG. 1 at 36 or a hook portion 38 as shown in FIG. 2, can either 1) lie along the axis so as to define a substantially linear element or 2) be angled relative to the longitudinal axis of the body portion 30. In this manner, the device can be adapted to various angulations between the bone connection surface and the rod 20. These embodiments of the invention provide either a thread or hook portion 36,38, respectively, having the upper tapered threaded portion about the U-shaped seat 16. Variability of angulation is eliminated as each unit would be a solid fix piece. But the assemblies can be individually made in various angulations. Such assemblies provide solid fixation of implants to the rod 20 where angulation is either not required or where known angulation may be repeatedly needed.

As stated above, the bone fixation element 12 can take on various shapes and sizes known in the art. The element 12 can have various configurations as a screw 36 and various thread designs. Also, as shown in FIG. 2, the hook portion 38 can be manufactured and used in a variety of hook sizes. Other shapes and sizes well known in the art can also be used.

The assembly is preferably made from machined titanium or alloy, but can be alternatively made from other types of cast or molded materials well known in the art.

Figure 3:
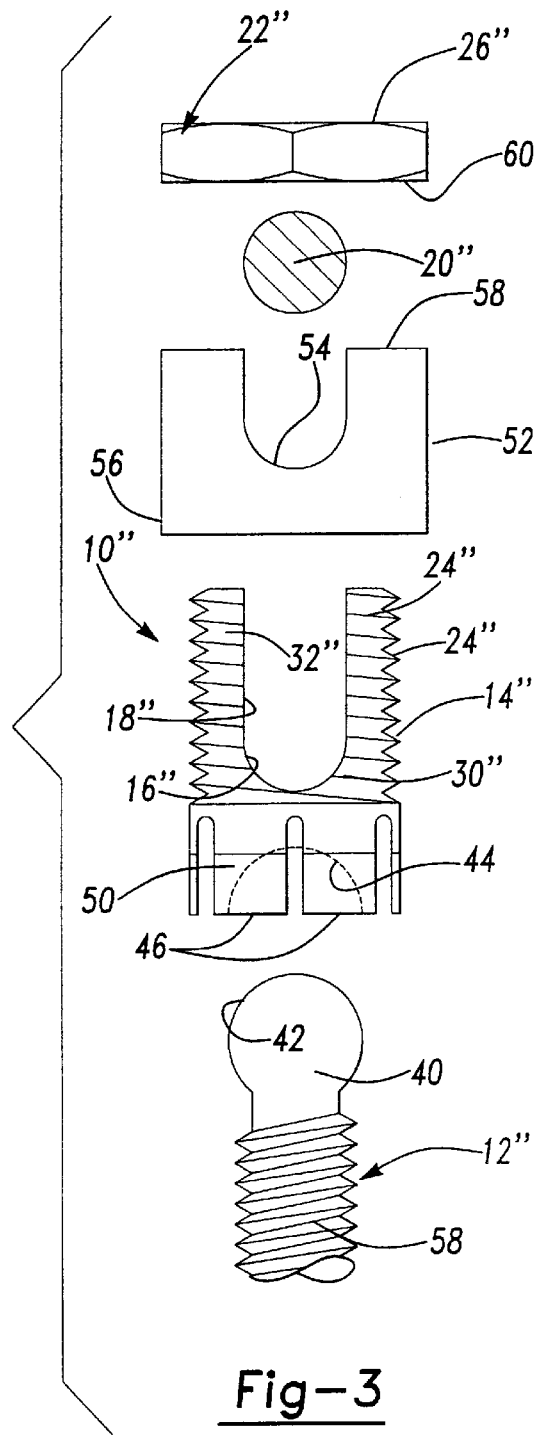
FIG. 3 is a side exploded view of a third embodiment of the present invention.
Figure 4:
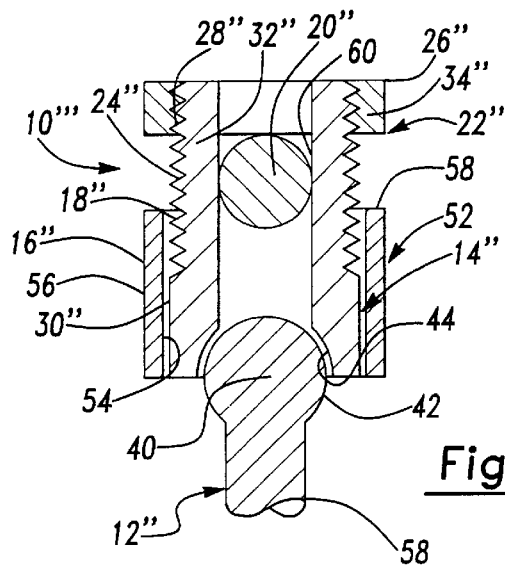
FIG. 4 is a cross sectional side view of the third embodiment of the present invention as assembled.

A second alternative embodiment of the present invention is shown in FIGS. 3 and 4. As stated above, double primed numbers are used to indicate like structure between the several embodiments.

Referring specifically to FIGS. 3 and 4, the bone fixation element 12" is shown as an independent screw member. The element 12" includes a head portion 40 having a substantially spherical outer surface 42. The rod receiving mechanism 14" is shown as a single integral unit including the first seat 16" for receiving the rod member 20" as discussed above between arms 32" and 34" and a second seating surface 44 having a substantially spherical shape for seating the head portion 40 of element 12" therein.

Referring more specifically to the rod receiving member 14", it consists of a substantially tubular body including the pair of spaced substantially parallel arms 32",34" extending therefrom and forming the substantially U-shaped seat 16" as discussed above. The tubular body further includes a socket portion defining the second seat 44 which includes outwardly flaring flanges 46, as best shown in FIG. 3. The outwardly flaring flanges 46 have distal ends which flare radially outwardly relative to a central axis of the rod receiving member 14. The outer surfaces 50 define the outer surface of the second seat 44.

The head portion 40 and/or the seat 44 can have a textured surface for better gripping of the spherical outer surface 42. The textural surface can take on various forms, such as ripples abrasions or the like, which increase the effective surface to surface contact and provide micro or macro grips against the outer surface 42.

The locking mechanism 22" of this embodiment includes the nut member 26" and a tubular sleeve member generally shown at 52. Although the nut member 26" and sleeve member 52 are shown as separate elements, the present invention could be practiced where the nut member 26" includes a skirt portion integrally extending therefrom. In either embodiment, the sleeve 52 locks and fixes the head portion 40 of the screw element 12" within the scat 44 prior to the nut member 26" locking and fixing the rod 20" within the seat 16". The sleeve member 52 includes an inner surface 54 which, upon being disposed over and about the outer surface 50 of the flanges 46, engages and inwardly deflects the distally outwardly tapering surfaces thereof to engage the socket portion of the seat 44 with the head portion 40 of the screw member 12". This can be accomplished prior to the connection of member 14" with the rod 20" and its locking in place by the nut member 26".

Referring more specifically to the sleeve member 52, it includes curved recessed portions 54 for seating of the rod member 20" therein in the assembled configuration as shown in FIG. 4. The sleeve 52 also includes a skirt portion 56 which is disposed about the flanges 46 in the assembled position, as shown in FIG. 4. In the embodiment shown in FIGS. 3 and 4, the element 30" includes the tapered threaded outer surface 24" which can be engaged by the threaded inner surface 28" of the nut member 26". As the nut member 26" is threaded over the outer tapered surface 24", it not only inwardly deflects the arms 32",34" to engage the rod member 20" but also forces the skirt portion 56 of the sleeve member 52 over the outwardly flared flanges 46 so as to force the inner surface of the seat 44 to frictionally engage and hold in a fixed manner the head portion 40 of the screw element 12". The screw element 12" is then locked securely at whatever angle the components are in. This locking is independent of the locking of the rod 20" in place.

This locking of the screw element can occur in two ways. The outer sleeve 52 can be pushed down with an instrument without the rod being in place or pushed down as the nut 26" is tightened over the rod 20". This gives the surgeon the option of adjusting the screw angle for abnormal anatomy and locking it prior to locking the rod 20" to the assembly 10" or, alternatively, locking the screw element 12" and rod 20" interfaces simultaneously when correction is not required.

As stated above, the head portion 40 is shown to be substantially spherical in shape. The seat 44 is a socket portion which is also substantially spherical for seating and engaging the head portion 40 therein. This allows for easy angular adjustment between the two components. Alternatively, the head portion 40 of the screw element 12" can take on various other shapes, such as a square shape, which may not allow for similar angulation but would allow for similar connection between the head portion 40 and the seat 44 in accordance with the present invention.

In the embodiment as shown wherein the head portion 40 is of a spherical shape for mating with the spherically shaped female seating portion 44, the configuration allows for up to 25° or more of angulation in all directions relative to the shaft portion 58 of the screw element 12". Thus, the present invention provides a multi-planar locking mechanism that allows for angulation in all planes. It also provides a locking mechanism that allows the mechanism to be locked at any angle prior to rod insertion. Further results of the above is that the invention provides a multi-planar locking mechanism that reduces intraoperative rod contouring provides flexibility.

With more specific regard to the locking mechanism, the sleeve ring 52 includes an edge surface 58. The nut member 26" includes an abutment surface 60 for abutting against the edge 58 as the nut member 26" is threaded onto the tapered threaded portion 24" to force the ring member 52 over the outer surface of the flanges 50.

In operation, the screw element 12" is fixed onto a bone, the head portion 40 extending from the bone surface. The rod seating member 14" is then disposed over the head portion 40 of the screw element 12" by insertion of the head portion 40 into the seat 44. This is a snapping operation but allows for angular adjustment of the tubular member 14" relative to the longitudinal axis of the screw element 12". The ring 52 is then disposed over the member 14" and an instrument is used to force the ring member 52 over the flanges 50 so as to lock the head portion 40 within the seat 44 thereby fixing the angulation between the two elements. The rod 20" is then seated within seat 16" of the member 14" as well as within the groove 54 of the ring 52. Finally, the nut member 26" is threaded over the tapered outer surface 24" of the arms 32",34" thereby fixing the rod 20" in frictional engagement within the seat 16" and against the nut member 26". Alternatively, as discussed above, the nut member 26" can be used to force the sleeve member 52 in place so as to lock the head 40 and screw member 12" relative to the element 14".

Utilizing the embodiment of the present invention as shown in FIGS. 1 and 2, the process is exactly the same with regard to locking the rod member 20 in place once the screw or hook portions 36,38, respectively, are connected to the known.

In view of the above, the present invention provides a method for locking a rod 20, 20" to a bone by the general steps of first fixing a rod seating member 14,14',14" to a bone and then seating a portion of the rod 20,20" within a substantially U-shaped seat 16,16" of the seating member 14,14',14". The rod 20,20" is locked within the U-shaped seat 16,16" while engaging and contouring at least a portion of the U-shaped seat 16,16" about the rod 20,20". As shown in FIGS. 3 and 4, this method can be more specifically defined by the steps of fixing the bone fixation member 12" to a bone and then locking and fixing the rod seating member 14" to the head portion 40 of the bone fixation member 12" and then locking the rod 20" within the U-shaped seat 16". The fixing step is accomplished by forcing the ring 52 over the outwardly flared portions 46 of the seat portion 44 to lock and fix the head portion 40 of the bone fixation element 12" therein. Finally, the locking of the rod is accomplished by locking the rod 20" within the U-shaped seat 16" by engaging the inner threaded surface 28" of the nut member 26" over the tapered outer threaded surface 24" of the U-shaped seat 16" to force the ring 52 over the outer surface 50 of the seat portion 44 to lock and fix the head portion 40 of the bone fixation clement 12" therein while simultaneously deforming the inner surface of the U-shaped seat 16" about the rod 20" seated therein.

Figure 5:
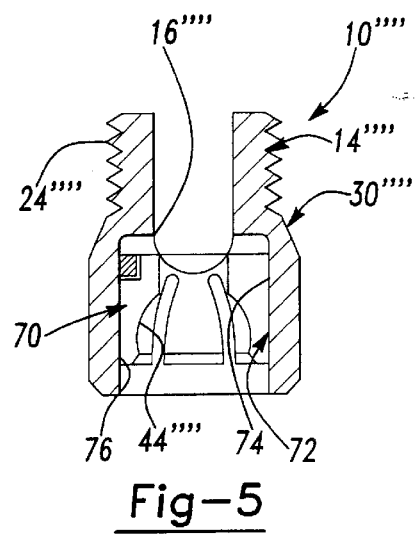
FIG. 5 is a cross sectional view of a further embodiment of the present invention.
Figure 6:
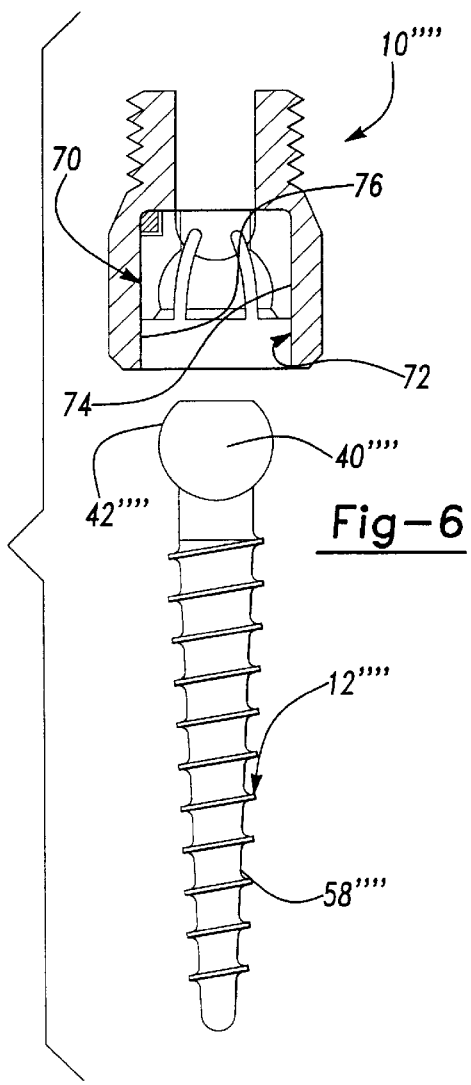
FIG. 6 is a cross sectional view of the forth embodiment of the present invention and a screw member disposed adjacent the assembly.
Figure 7:
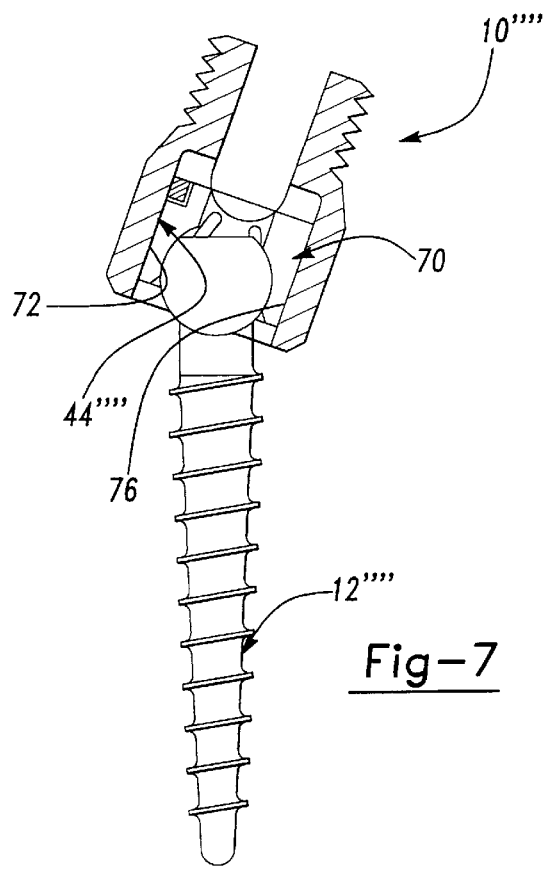
FIG. 7 shows the screw member inserted into the pocket of the forth embodiment of the present invention.
Figure 8:
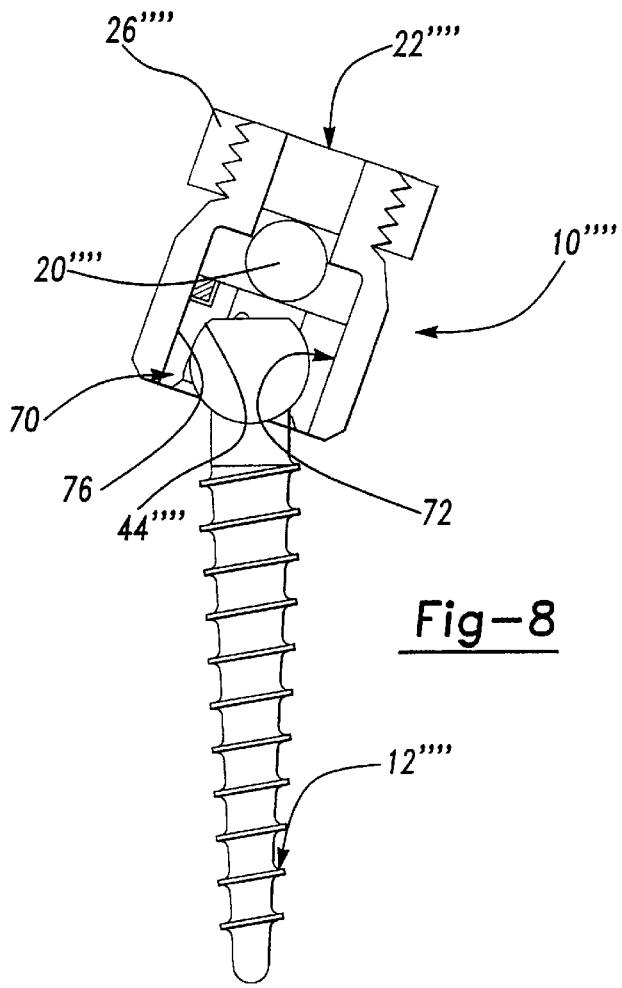
FIG. 8 shows the screw member and a rod member locked within the assembly, the assembly being shown in cross section.

A further embodiment of the present invention is shown in FIGS. 5–8. This embodiment of the invention includes the bone fixation element generally shown at 12"", this embodiment being characterized by including a screw head receiving insert generally shown at 70 which is moveable within the assembly 10"" between a locked position as shown in FIGS. 7 and 8 entrapping the screw head 40"" therein and an unlocked position wherein the screw head 40"" enters or escapes, as shown in FIGS. 5 and 6. That is, this embodiment of the invention includes a single unit capable of receiving a screw head 40"" therein and then allowing for polyaxial adjustment of the screw head relative to the assembly and then locking of the screw head within the assembly without requirement of additional elements to the assembly. This embodiment of the invention drastically reduces surgical time in spinal surgery and simplifies the elements needed for implementing the bone fixation. Such a system is particularly useful when the rod 20"" in not lined up with the screw 12"".

More specifically, the assembly 10"' includes a body 30"" including an internal portion 72"". The internal portion 12"" generally includes a first portion 74 which is radially outwardly recessed relative to a second internal portion 76. The internal portion 74 can be effectively recessed or actually recessed. The first portion could have a greater diameter than the second portion or the second portion could be formed by flanges that extend radially internally from an inner surface of the second portion thereby effectively defining the end of each flange as the radially inwardly extending surface.

The screw head receiving means 70 consists of a insert member 70 including a seat 44"" for seating the screw head 40"" therein. The insert 70 is moveable within the internal portion 72 between the locked and unlocked position as discussed below.

Figure 9:
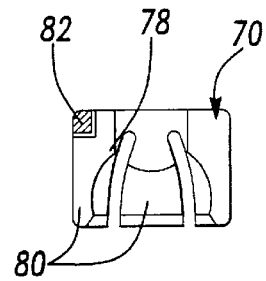
FIG. 9 shows a side view, and cross section of the insert member.

FIG. 9 shows an enlarged cross-sectional view of the insert 70 made in accordance with the present invention. The seat 44"" more particularly includes a base portion 78 and a plurality of flexible arms 80 extending therefrom combining with the base portion 78 to form a pocket. The arms 80 define flexible walls of the pocket extending from the base portion 78.

At least one of the arms 80 includes a hinged portion 82 allowing for outward deflection of the arm 80. The hinged portion, as shown in FIG. 9, can be a recess cut into the base portion 78 adjacent the arm 80 to allow for increase outward flexibility of the arm 80 which includes the hinged portion 82. This allows for increased ease of insertion of the screw head 40""into the pocket.

FIGS. 5–8 sequentially show the method of using the present invention for fixing a polyaxial screw 12"" therein. The screw itself 12"" is inserted into the bone by itself. This provides excellent visualization of screw placement since the larger body/insert assembly 10"" is pushed on the screw head after screw insertion into the bone.

As shown in FIG. 5, the insert 70 is sufficiently collapsible to be snapped into the internal portion 72 of the body element 34"". This is accomplished by compressing the insert 70 and releasing it inside the internal portion 72. The assembly itself can be made from any durable material, such as carbon composites, nitinol, stainless steel, composite materials, plastics and plastic compositions or even resorbable materials. Preferably, titanium is used to minimize artifacts from x-rays and other diagnostic imaging systems. The combined assembly effectively provides the equivalent of a one piece assembly which is a significant improvement over prior art two piece assemblies or multiple piece assemblies necessary for only securing a screw head within a fixation device.

When the insert 7 is disposed within the first portion 74 of the internal portion 72, there is internal space to allow for slight expansion of the insert 70 therein. When the screw head 40"" is disposed into the internal portion 72, the screw head 40"" will effectively force the insert 70 into the first portion 74 thereby ensuring the ability of the pocket to expand sufficiently to allow insertion of the screw head 40"" into the pocket. Once the screw head 40"" is fully inserted into the pocket, the insert 70 snaps onto the screw head 40"". In this condition, polyaxial movement can be achieved.

Locking can be achieved in two manners. The body 30"" can be pulled up relative to the screw 12"" with an instrument (not shown) without the rod 20"" being in placed or pulled by the nut 26"" as the nut 26"" is tightened over the rod 20"". This provides the surgeon with the option of adjusting the screw angle for abnormal anatomy and locking it prior to locking the rod 20"" to the assembly 10"" or locking the screw 12"" and rod 20"" interfaces simultaneously when correction is not required.

Figure 10:
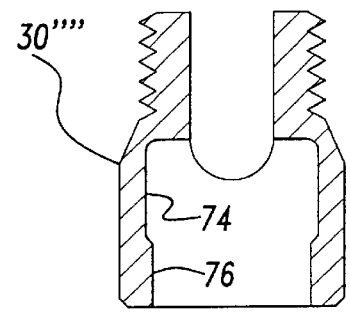
FIG. 10 shows a cross sectional view of the body portion of the forth embodiment of the present invention.

As shown in FIG. 8, the U-shaped inner surface defining the seat portion 16"" extends into the internal portion 72. Upon seating of the rod 20"", the inserted portion of the rod 20"", contacts a portion of the surface of the base portion 80 of the insert 70 for final seating of the insert 70 within the second portion 76 of the internal portion 72. As best shown in FIG. 10, which shows a cross section of the body portion 30"", the second portion 76 includes a radially inwardly tapering surface. Thus, as the insert 70 is drawn into the second portion 76, the outer surface of the arms 80 of the insert 70 are progressively compressed about the screw head 40"" thereby effectively engaging and locking the screw head 40"" in position relative to the body portion 30"". Upon final locking of the rod 20"" within the assembly 10"", as described above, complete fixation is achieved.

Also significant with regard to this embodiment is the fact that the nut 26"", which includes a tapered treaded internal surface as discussed above, compresses the tapered threaded portion 14"" of the assembly 10"" against the rod 20"". The nut 26"" will also seat against the rod 20"", but the surface area engaging the rod 20"" will be vastly increased over the prior art, which increases the assembly to rod holding power. In fact, the nut against the rod is only a secondary locking means. The force of the portions 14"" against the rod 20"" is the primary locking mechanism. In other words, the rod 20"" is engaged by the nut 26"", the body portion 30"", and the insert 70. Effective engagement of the insert 70 is significant as demonstrated in FIGS. 11 and 12.

Figure 11:
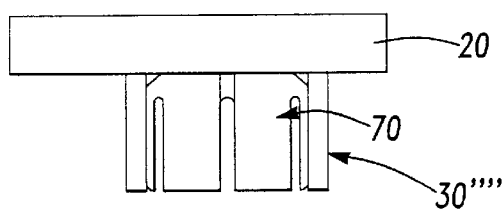
FIG. 11 shows a cross sectional view of the assembly having straight rod disposed therein.
Figure 12:
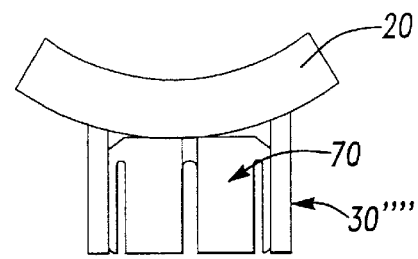
FIG. 12 shows a cross section of the assembly having a curved rod disposed therein.

FIG. 11 shows a cross section of the assembly wherein a straight rod 20 is retained within the assembly. With such a straight rod 20, the rod 20 will push the insert 70 down until the rod 20 fits within the U-shaped channel of the body 30"". It is ideal for the rod 20 to contact the edges of the body 30"" inside the U-shaped channel for maximum rod gripping strength. When the rod 20 is contoured, as shown in FIG. 12, the insert 70 of the present embodiment can self-adjust and be pushed downward further then the edges of the body 30"" within the U-shaped cut-out to maximize rod contact. Such self adjustment is not at all found in the prior art since such U-shaped cut-outs in a body portion are fixed machine surfaces.

Figure 13:
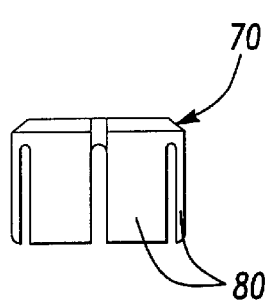
FIG. 13 is side view of the insert member of the forth embodiment of the present invention.
Figure 14:
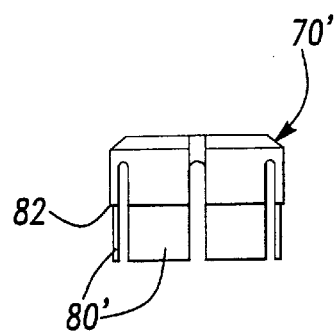
FIG. 14 shows a side view of a second embodiment of the insert member.
Figure 15:
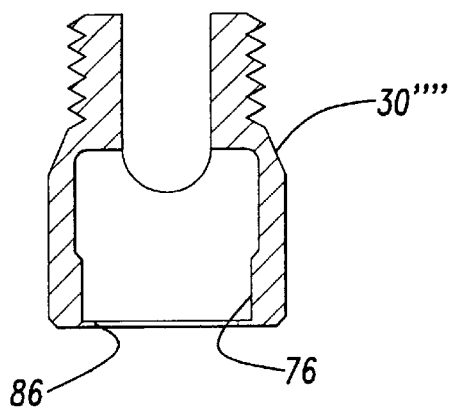
FIG. 15 shows a cross sectional view of a second embodiment of the body portion of the forth embodiment.
Figure 16:
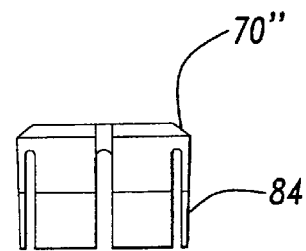
FIG. 16 is a side view of a third embodiment of the insert.
Figure 17:
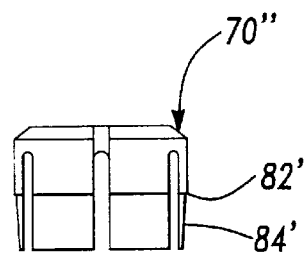
FIG. 17 is a side view of a forth embodiment of the insert combining the embodiment of the insert combining the embodiment shown in FIGS. 14 and 16.

FIGS. 13–18 shown various permutations of the insert and body portions of the present invention. FIG. 13 shows an insert 70 including arms 80 having smooth outside surfaces. This is an embodiment which is shown in the previously discussed figures. In FIG. 14, the insert 70" includes arms 80" having an stepped outer surface 82. Such a step outer surface provides a stop for engaging the inner surface of the internal portion 72 to prevent the insert 70" from moving beyond the desired engagement location. FIG. 16 shows an insert 70" including a radially inwardly tapered outer surface portion 84 for progressive engagement with the second portion 72. FIG. 17 shows a further embodiment of the insert 70" combining the inward tapered surface 84" with the step 82".

Figure 18:
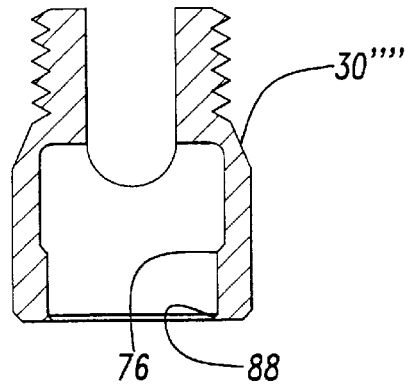
FIG. 18 is a cross sectional view of the third embodiment of the body portion.

FIG. 15 shows a body portion 30"" wherein the second portion 76 includes a radially inwardly extending lip 86 at the peripheral edge thereof. FIG. 18 shows a chamfered surface 88 a the peripheral edge of the second portion 76. both the lip 86 or the chamfered portion 88 provide further stops to ensure that once the insert member 70 is disposed within the internal portion 72, the insert 70 does not inadvertently exit therefrom.

The components for the assembly can be manufactured according to the following techniques, but every manufacturer has their own variations.

The body is made by first blanking the outer shape from round bar stock. By holding on the threaded end, or an extension to the threaded end (extra bar material), a hole is made into the opposite end. This hole is undersize relative to the taper to allow the taper to be but with a single tool. While the part turns in a lathe, a boring bar having a small cutting tip is introduced into the hole and the taper and recess cut. The threads are then cut, any extension cut off, and the slot either milled or cut be more EDM.

The insert is made by cutting the outside cylindrical shape with an extension to hold on in a lathe. A hole is drilled into one end and a boring bar with a small cutting tip used to enter the hole and cut the spherical seat. The outer slots and hinge details are cut by either a slitting saw or a wire EDM.

Another possibility for the insert is to have a U cut or indentation in the top of it for seating of the rod. This is not preferable, since orientation of the insert would then be necessary, but possible.

Another addition to the body at the threaded portion is to add a recess in the side of the arms of the U on the inside for a rod to fit within. This would act as a guide for seating the nut with an instrument, as it would align the nut relative to the threads.

In combination, this last described embodiment provides a novel fixation assembly which can be either combined with the novel rod retaining features described above or with other types of rod retaining features resulting in a simple effective and efficient means for fixing a screw member to a rod.

In accordance with this method, the locking mechanism is locked to the spherical head 40 of the bone fixation element 12" at a desired angle prior to rod insertion or locked simultaneously by tightening of the nut member 26". This locking method and the mechanism used therewith is fully reversible and top loading.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically describe.

What is claimed is:

1. A spinal implant fixation assembly (10) comprising: bone fixation means (12) for fixation of the assembly (10) to a support; rod receiving means (14) operatively connected to said bone fixation means (12) and including a first seat (16) having an inner wall (18) for seating a portion of a rod (20) therein; and locking means (22) engaging said rod receiving means (14) for forcing said inner wall (18) to contour around and engage the rod (20) seated therein and for locking and fixing the rod (20) relative to said assembly (10), said rod receiving means (14) including a tapered outer surface (24), said locking means (22) including an inner surface for being forced over and engaging said outer tapered surface (24) and inwardly deflecting said rod receiving means (14) about said first seat (16) as said locking means (22) further engages said tapered outer surface (14).

2. An assembly as set forth in claim 1 wherein said tapered outer surface (24) is further defined as a tapered threaded surface (24), said locking means (22) including an inner threaded surface (20).

3. An assembly as set forth in claim 2 wherein said rod receiving means (14) includes a body portion (30) having two arms (32,34) extending therefrom and being substantially parallel relative to each other, said two arms (32,34) and body portion (30) forming a U-shaped inner surface defining said first seat, said arms (32,34) including said tapered threaded surface (24).

4. An assembly as set forth in claim 1 wherein said fixation means is further defined as bone fixation means for fixing said assembly (10) to a bone.

5. An assembly as set forth in claim 4 wherein said body portion (30) includes said bone fixation means (12) extending therefrom at a predetermined angle relative to said U-shaped inner surface (18) defining said first seat (16).

6. An assembly as set forth in claim 5 wherein said bone fixation means (12) includes a hook portion (38) extending from said body portion (30') and being integral therewith.

7. An assembly as set forth in claim 5 wherein said bone fixation means includes a screw portion (36) extending from said body portion (30) and being integral therewith.

8. A spinal implant fixation assembly (10) comprising: bone fixation means (12) for fixation of the assembly (10) to a support; rod receiving means (14) operatively connected to said bone fixation means (12) and including a first seat (16) having an inner wall (18) for seating a portion of a rod (20) therein; and locking means (22) engaging said rod receiving means (14) for forcing said inner wall (18) to contour around and engage the rod (20) seated therein and for locking and fixing the rod (20) relative to said assembly (10), said bone fixation means being defined as bone fixation means for fixing said assembly to a bone, said bone fixation means (12") including a head portion (40), said rod receiving means (14") including a second seat (44) for seating said head portion (40) therein, said second seat (44) including an outer surface (50) thereabouts, said locking means (22") including a skirt engaging and radially inwardly deflecting said outer surface of said second seat portion (42) for first locking and fixing said head portion (40) within said second seat (44)

prior to said locking means (22") locking and fixing the rod (20") within the first seat (16").

9. An assembly as set forth in claim 8 wherein said rod receiving means (14") consists of a substantially tubular body including a pair of spaced, substantially parallel arms (32",34") extending therefrom and forming a substantially U-shaped seat defining said first seat (16"), said tubular body further including a socket portion including outwardly flaring flanges (46) having distal end portions flaring radially outwardly tapering surfaces (50) relative to a central axis of said rod receiving means defining said outer surface (50) of said second seat (44), said skirt portion (52) engaging and inwardly deflecting said distally outwardly tapering surfaces to engage said socket portion with said head portion (40).

10. An assembly as set forth in claim 9 wherein said locking means includes a ring member (52) defining said skirt portion, said tapered outer surface (24") of said rod receiving means (12") being a tapered threaded surface, said locking means (22") further including a nut member (26") including an inner threaded surface (28") for engaging and inwardly deflecting said tapered threaded surface (24").

11. An assembly as set forth in claim 10 wherein said head portion (40) is substantially spherical, said socket portion being substantially spherical for seating and engaging said head portion (40) therein.

12. An assembly as set forth in claim 10 wherein said ring (52) includes an edge surface (58), said nut member (26") including an abutment surface (60) for abutting against said edge surface (58) as said nut member (26") is threaded onto said tapered threaded portion (24") to force said ring member (52) over said outer surface of said socket portion.

13. An assembly is set forth in claim 8 wherein said second seat (44) includes gripping means for gripping said head portion (40) within said second seat (44).

14. A spinal implant fixation assembly (10) comprising: bone fixation means (12) for fixation of the assembly (10) to a support; rod receiving means (14) operatively connected to said bone fixation means (12) and including a first seat (16) for seating a portion of a rod therein; and self-locking means (22) disposed about said rod receiving means (14) for securing and self-locking the rod (20) seated within said first seat (16) and fixing the rod (20) relative to said assembly (10), said self-locking means including an outer tapered surface (24) of said rod receiving means (14) and a nut member (26) having an inner surface for being forced over and engaging said outer tapered surface (24).

15. An assembly as set forth in claim 14 wherein tapered outer surface (24) is further defined as a tapered thread surface (24) said nut member (26) including an inner threaded surface (20).

16. A spinal fixation assembly 10"" comprising: a screw head receiving means 70 for retaining a head 40"" of a screw 12"" therein, said screw head receiving means 70 being movable within said assembly 10"" between a locked position entrapping the screw head 10"" and an unlocked position wherein the screw head 10"" enters or escapes, said assembly 10"" including a body portion 30"" including an internal portion 72, said screw head receiving means 70 including an insert member including a seat 44"" for seating the screw head 40"" therein, said insert member being movable within said internal portion 72 between said locked and unlocked positions, said body portion 30"" includes rod retaining means for retaining a rod therein, said internal portion 72 including a first portion adjacent to said rod retaining means and a second portion extending from said first portion, said first portion having an inner surface recessed radially outwardly relative to said second portion.

17. An assembly as set forth in claim 16 wherein said assembly 10"" includes a body 30"" including an internal position 72, said screw head receiving means 70 including an insert member including a seat 44"" for seating the screw head 40"" therein, said insert being movable within said internal position 72 between said locked and unlocked positions.

18. An assembly as set forth in claim 16 wherein said seat 44"" includes a base portion 78 and a plurality of flexible arms 80 extending therefrom combining with said base position 78 to form a pocket, said arms 80 defining flexible walls of said pocket extending from said base portion 78.

19. An assembly as set forth in claim 18 wherein at least one of said arms 80 includes a hinge portion 82 for allowing outward deflection thereof.

20. An assembly as set forth in claim 19 wherein said internal portion includes stop means for engaging an outer surface of said arms 80 to retain said insert member within said internal portion.

21. An assembly as set forth in claim 16 wherein said second portion includes a radially inwardly extending lip at an end thereof most distal relative to said first portion.

22. An assembly as set forth in claim 16 wherein said second portion includes an end edge most distal relative to said first portion, said end edge being chamfered radially thereabout.

23. An assembly as set forth in claim 16 wherein said arms of said insert member includes an outer surface including engagement means for engaging an inner surface of said internal portion.

24. An assembly as set forth in claim 23 wherein said internal portion includes an annular shoulder between said first and second portions, said outer surface of said arms including a step defining said engagement means for engaging said shoulder to prevent said insert from moving beyond a desired engagement location.

25. An assembly as set forth in claim 24 wherein said arms have an outer surface tapering inwardly away from said step.

26. An assembly as set forth in claim 23 wherein said arms have an outer surface tapering inwardly away from said base portion.

27. An assembly as set forth in claim 23 wherein said body includes a neck portion, said rod retaining means including two opposed U-shaped seats extending into said neck portion, said U-shaped seat having a bottom portion thereof extending into said internal portion such that a rod seated in said U-shaped seat abuts against said insert member disposed within said first portion and frees said insert member into said second portion, said outer walls of said arms engaging and being forced radially inwardly by said second portion to collapse and engage a screw head disposed within said pocket.

28. A method of retaining a screw head in a spinal fixation assembly by;
   inserting a screw head into a pocket of an insert is an expanded condition contained within a first portion of an internal portion of a body member wherein the internal portion includes the first portion which is radially outwardly recessed relative to a second portion and;
   disposing a portion of a rod member into a seat portion of the body member, abutting the disposed portion of the rod member against the insert member which is disposed in the first portion in the expanded condition;
   moving the insert into the second portion, so that the pocket of the insert assumes a contracted condition to fixedly engage the screw head within the pocket, the rod member locking the insert in the second portion.

29. A method as set forth in claim 28 further including the steps of inserting a non-straight portion of the rod into the seat portion and further compressing the insert member into the first portion.

* * * * *